(12) United States Patent
Doeberitz et al.

(10) Patent No.: US 9,145,444 B2
(45) Date of Patent: Sep. 29, 2015

(54) COMPOUNDS AND METHODS ASSOCIATED WITH DIFFERENTIAL METHYLATION OF HUMAN PAPILLOMA VIRUS GENOMES IN EPITHELIAL CELLS

(75) Inventors: Magnus Von Knebel Doeberitz, Heidelberg (DE); Svetlana Vinokurova, Heiligkreuzsteinach (DE)

(73) Assignee: Ruprecht-Karls-Universität Heidelberg, Heidelberg (DE)

( * ) Notice: Subject to any disclaimer, the term of this patent is extended or adjusted under 35 U.S.C. 154(b) by 771 days.

(21) Appl. No.: 12/740,986

(22) PCT Filed: Oct. 31, 2008

(86) PCT No.: PCT/EP2008/009197
§ 371 (c)(1),
(2), (4) Date: Jul. 7, 2010

(87) PCT Pub. No.: WO2009/062604
PCT Pub. Date: May 22, 2009

(65) Prior Publication Data
US 2010/0279975 A1    Nov. 4, 2010

Related U.S. Application Data

(60) Provisional application No. 60/984,977, filed on Nov. 2, 2007.

(51) Int. Cl.
| | | |
|---|---|---|
| *A61K 31/7068* | (2006.01) | |
| *A61K 31/353* | (2006.01) | |
| *C12N 7/00* | (2006.01) | |
| *C07K 14/005* | (2006.01) | |
| *A61K 31/166* | (2006.01) | |
| *A61K 31/245* | (2006.01) | |
| *A61K 31/502* | (2006.01) | |
| *A61K 31/706* | (2006.01) | |

(52) U.S. Cl.
CPC ............ *C07K 14/005* (2013.01); *A61K 31/166* (2013.01); *A61K 31/245* (2013.01); *A61K 31/353* (2013.01); *A61K 31/502* (2013.01); *A61K 31/706* (2013.01); *A61K 31/7068* (2013.01); *C12N 7/00* (2013.01); *C12N 2710/20022* (2013.01)

(58) Field of Classification Search
CPC .................... A61K 31/7068; A61K 31/353
See application file for complete search history.

(56) References Cited

U.S. PATENT DOCUMENTS

2006/0128654 A1* 6/2006 Tang et al. ............... 514/49
2010/0285443 A1* 11/2010 Esteller ..................... 435/5

FOREIGN PATENT DOCUMENTS

| CA | 2 039 643 | 11/1991 |
|---|---|---|
| JP | 2002-534377 | 10/2002 |
| JP | 2007-505045 | 3/2007 |
| WO | WO 00/33832 | 6/2000 |
| WO | WO 00/40228 | 7/2000 |
| WO | WO 2005/025503 A2 | 3/2005 |
| WO | WO2008/024844 A2 | 2/2008 |
| WO | WO 2008/027049 A1 | 3/2008 |
| WO | WO2008/071998 A2 | 6/2008 |

OTHER PUBLICATIONS

Kaminskas et al. The Oncologist, 2005, 10(3), p176-182.*
Woodman et al., Nature Reviews Cancer, Jan. 2007, 7, p11-22.*
Kalantari et al., Virology, 2008, 374, p292-303.*
Niwa et al.. "Topical Vidarabine or 5-Fluorouracil Treatment Against Persistent HPV in Genital (pre)cancerous Lesions," pp. 1437-1441 (2003).
Kalantari, Mina et al., "Conserved methylation patterns of human papillomavirus type 16 DNA in asymptomatic infection and cervical neoplasia", Journal of Virology, The American Society for Microbiology, US, vol. 78, No. 23, Dec. 1, 2004, pp. 12762-12772.
Badal, V. et al., "CpG methylation of human papillomavirus type 16 DNA in cervical cancer cell lines and in clinical specimens: Genomic hypomethylation correlates with carcinogenic progression", Journal of Virology, The American Society for Microbiology, US, vol. 77, No. 11, Jun. 1, 2003, pp. 6227-6734.
Badal, S. et al., "The human papillomavirus-18 genome is efficiently targeted by cellular DNA methylation ", Virology, Academic Press Orlando, US, vol. 324, No. 2, Jul. 1, 2004, pp. 483-492.
Bhattacharjee, Bornali et al., "CpG methylation of HPV 16 LCR at E2 binding site proximal to P97 is associated with cervical cancer in presence of intact E2", Virology, vol. 354. No. 2, Oct. 25, 2006, pp. 280-285.
Kim, K. et al., "Methylation patterns of papillomavirus DNA, its influence on E2 function, and implications in viral infection", Journal of Virology, The American Society for Microbiology, US, vol. 77, No. 23, Dec. 1, 2003, pp. 12450-12459.
Vilkaitis, Giedrius et al., "Processive methylation of hemimethylated CpG sites by mouse Dnmtl DNA methyltransferase", The Journal of Biological Chemistry, vol. 280, No. 1, Jan. 7, 2005, pp. 64-72.
International Search Report for PCT/EP2008/009197, mailed Dec. 22, 2009.
Extended European Search Report cited in related European Patent Application No. 11172852.3, dated Apr. 25, 2012.
Notice of Reasons for Rejection issued in related Japanese Patent Application No. 2010-531461, dated May 29, 2013.

* cited by examiner

*Primary Examiner* — Jonathan S Lau
(74) *Attorney, Agent, or Firm* — Foley & Lardner LLP

(57) ABSTRACT

The invention relates to compounds and methods useful in detection and therapy of HPV-associated diseases. The invention is based on the elucidation of a mechanism by which replication of HPVs occurs in naturally infected tissues and cells. Moreover it is based on the identification of distinct epigenetic changes of the viral genome in infected cells that allows promotion of the affected cells to precancerous and cancerous cells. The invention therefore provides methods of diagnosing neoplasias and their precursor lesions as well as methods of preventing the development of malignancies or inhibiting tumor growth.

8 Claims, 6 Drawing Sheets

Vinokurova et al., manuscript in preparation.

E2BS1 methylation

SEQUENCE LISTING

```
<160> NUMBER OF SEQ ID NOS: 27

<210> SEQ ID NO 1
<211> LENGTH: 12
<212> TYPE: DNA
<213> ORGANISM: Artificial
<220> FEATURE:
<223> OTHER INFORMATION: Synthetic Construct

<400> SEQUENCE: 1
accgaattcg gt                                                           12

<210> SEQ ID NO 2
<211> LENGTH: 12
<212> TYPE: DNA
<213> ORGANISM: Artificial
<220> FEATURE:
<223> OTHER INFORMATION: Synthetic Construct

<400> SEQUENCE: 2
accgatttgg gt                                                           12
```

```
<210> SEQ ID NO 3
<211> LENGTH: 12
<212> TYPE: DNA
<213> ORGANISM: Artificial
<220> FEATURE:
<223> OTHER INFORMATION: Synthetic Construct

<400> SEQUENCE: 3
accgaaatcg gt                                                         12

<210> SEQ ID NO 4
<211> LENGTH: 12
<212> TYPE: DNA
<213> ORGANISM: Artificial
<220> FEATURE:
<223> OTHER INFORMATION: Synthetic Construct

<400> SEQUENCE: 4
accgaaaccg gt                                                         12

<210> SEQ ID NO 5
<211> LENGTH: 20
<212> TYPE: DNA
<213> ORGANISM: Artificial
<220> FEATURE:
<223> OTHER INFORMATION: Synthetic Construct

<400> SEQUENCE: 5
cttgccatgc gtgccaaatc                                                 20

<210> SEQ ID NO 6
<211> LENGTH: 17
<212> TYPE: DNA
<213> ORGANISM: Artificial
<220> FEATURE:
<223> OTHER INFORMATION: Synthetic Construct

<400> SEQUENCE: 6
aatcactatg cgccaac                                                    17

<210> SEQ ID NO 7
<211> LENGTH: 11
<212> TYPE: DNA
<213> ORGANISM: Artificial
<220> FEATURE:
<223> OTHER INFORMATION: Synthetic Construct

<400> SEQUENCE: 7
tacataccgc t                                                          11

<210> SEQ ID NO 8
<211> LENGTH: 8
<212> TYPE: DNA
<213> ORGANISM: Artificial
<220> FEATURE:
<223> OTHER INFORMATION: Synthetic Construct

<400> SEQUENCE: 8 taagggcg                                                               8

<210> SEQ ID NO 9
<211> LENGTH: 12
<212> TYPE: DNA
<213> ORGANISM: Artificial
<220> FEATURE:
<223> OTHER INFORMATION: Synthetic Construct
```

```
<400> SEQUENCE: 9
attgaatttg gt                                                          12

<210> SEQ ID NO 10
<211> LENGTH: 12
<212> TYPE: DNA
<213> ORGANISM: Artificial
<220> FEATURE:
<223> OTHER INFORMATION: Synthetic Construct

<400> SEQUENCE: 10
attgatttgg gt                                                          12

<210> SEQ ID NO 11
<211> LENGTH: 12
<212> TYPE: DNA
<213> ORGANISM: Artificial
<220> FEATURE:
<223> OTHER INFORMATION: Synthetic Construct
<220> FEATURE:
<221> NAME/KEY: Misc_feature
<222> LOCATION: (1)..(12)

<400> SEQUENCE: 11
attgaaattg gt                                                          12

<210> SEQ ID NO 12
<211> LENGTH: 12
<212> TYPE: DNA
<213> ORGANISM: Artificial
<220> FEATURE:
<223> OTHER INFORMATION: Synthetic Construct

<400> SEQUENCE: 12
attgaaattg gt                                                          12

<210> SEQ ID NO 13
<211> LENGTH: 20
<212> TYPE: DNA
<213> ORGANISM: Artificial
<220> FEATURE:
<223> OTHER INFORMATION: Synthetic Construct

<400> SEQUENCE: 13
tttgttatgt gtgttaaatt                                                  20

<210> SEQ ID NO 14
<211> LENGTH: 17
<212> TYPE: DNA
<213> ORGANISM: Artificial
<220> FEATURE:
<223> OTHER INFORMATION: Synthetic Construct

<400> SEQUENCE: 14
aattattatg tgttaat                                                     17

<210> SEQ ID NO 15
<211> LENGTH: 11
<212> TYPE: DNA
<213> ORGANISM: Artificial
<220> FEATURE:
<223> OTHER INFORMATION: Synthetic Construct

<400> SEQUENCE: 15
tatatattgt t                                                           11
```

```
<210> SEQ ID NO 16
<211> LENGTH: 8
<212> TYPE: DNA
<213> ORGANISM: Artificial
<220> FEATURE:
<223> OTHER INFORMATION: Synthetic Construct

<400> SEQUENCE: 16 taagggtg                                                                    8

<210> SEQ ID NO 17
<211> LENGTH: 21
<212> TYPE: DNA
<213> ORGANISM: Artificial
<220> FEATURE:
<223> OTHER INFORMATION: Description of the artificial sequence: Primer

<400> SEQUENCE: 17
tttgtatgtg tttgtatgtg t                                                    21

<210> SEQ ID NO 18
<211> LENGTH: 23
<212> TYPE: DNA
<213> ORGANISM: Artificial
<220> FEATURE:
<223> OTHER INFORMATION: Description of the artificial sequence: Primer

<400> SEQUENCE: 18
ttaaaccata attactaaca taa                                                  23

<210> SEQ ID NO 19
<211> LENGTH: 22
<212> TYPE: DNA
<213> ORGANISM: Artificial
<220> FEATURE:
<223> OTHER INFORMATION: Description of the artificial sequence: Primer

<400> SEQUENCE: 19
acattttata ccaaaaaaca ta                                                   22

<210> SEQ ID NO 20
<211> LENGTH: 25
<212> TYPE: DNA
<213> ORGANISM: Artificial
<220> FEATURE:
<223> OTHER INFORMATION: Description of the artificial sequence: Primer

<400> SEQUENCE: 20
tagttttatg ttagtaatta tggtt                                                25

<210> SEQ ID NO 21
<211> LENGTH: 22
<212> TYPE: DNA
<213> ORGANISM: Artificial
<220> FEATURE:
<223> OTHER INFORMATION: Description of the artificial sequence: Primer

<400> SEQUENCE: 21 attaaccttaa aaatttaaa cc                                                   22

<210> SEQ ID NO 22
<211> LENGTH: 22
<212> TYPE: DNA
<213> ORGANISM: Artificial
<220> FEATURE:
<223> OTHER INFORMATION: Description of the artificial sequence: Primer
```

-continued

```
<400> SEQUENCE: 22
aaaaatttaa accttatacc aa                                              22

<210> SEQ ID NO 23
<211> LENGTH: 20
<212> TYPE: DNA
<213> ORGANISM: Artificial
<220> FEATURE:
<223> OTHER INFORMATION: Description of the artificial sequence: Primer

<400> SEQUENCE: 23
ttgtatgtgt ttgtatgtgt                                                 20

<210> SEQ ID NO 24
<211> LENGTH: 22
<212> TYPE: DNA
<213> ORGANISM: Artificial
<220> FEATURE:
<223> OTHER INFORMATION: Description of the artificial sequence: Primer

<400> SEQUENCE: 24
ggtttaaatt tttaaggtta at                                              22

<210> SEQ ID NO 25
<211> LENGTH: 24
<212> TYPE: DNA
<213> ORGANISM: Artificial
<220> FEATURE:
<223> OTHER INFORMATION: Description of the artificial sequence: Primer

<400> SEQUENCE: 25
acaactctat acataactat aata                                            24

<210> SEQ ID NO 26
<211> LENGTH: 23
<212> TYPE: DNA
<213> ORGANISM: Artificial
<220> FEATURE:
<223> OTHER INFORMATION: Description of the artificial sequence: Primer

<400> SEQUENCE: 26
aattgtgttg tggttattta ttg                                             23

<210> SEQ ID NO 27
<211> LENGTH: 24
<212> TYPE: DNA
<213> ORGANISM: Artificial
<220> FEATURE:
<223> OTHER INFORMATION: Description of the artificial sequence: Primer

<400> SEQUENCE: 27
caaatttaaa ccataattac taac                                            24
```

COMPOUNDS AND METHODS ASSOCIATED WITH DIFFERENTIAL METHYLATION OF HUMAN PAPILLOMA VIRUS GENOMES IN EPITHELIAL CELLS

This application is a National Stage of International Application PCT/EP2008/009197, filed Oct. 31, 2008, published May 22, 2009, under PCT Article 21(2) in English; which claims the priority of U.S. Patent Application No. 60/984,977, filed Nov. 2, 2007.

FIELD OF THE INVENTION

The invention relates to compounds and methods useful in detection and therapy of HPV-associated diseases. The invention is based on the elucidation of a mechanism by which replication of HPVs occurs in naturally infected tissues and cells. Moreover it is based on the identification of distinct epigenetic changes of the viral genome in infected cells that allows promotion of the affected cells to precancerous and cancerous cells. The invention therefore provides methods of diagnosing neoplasias and their precursor lesions as well as methods of preventing the development of malignancies or inhibiting tumor growth.

BACKGROUND OF THE INVENTION

The phenotype of single normal cells is in the human body is defined by the set of genes that are expressed at a certain time point. These gene expression patterns define the combination and individual levels of proteins that provide structure and function to all living cells and at a level of higher complexity all organs. Differentiation processes that are essential for all organs to function appropriately are also regulated by shifts in the level and combination of individual genes. Differential gene expression patterns determine the status of a cell for example as a stem cell that give rise to progenies that can undergo differentiation to fully differentiated cells, with substantially changed gene expression patterns. These finally conclude their lifespan by again changing their gene expression pattern and thereby adopting properties of aging and finally dying cells. Although the molecular control of these processes are far from being solved several lines of evidence suggest that substantial parts of this control is mediated by distinct methylation of certain GpC-islands within the human genome.

Conceptually the addition of methyl-$(C(H)_3)$-groups to the certain nucleotides within the cell's genome results in a condensed and tightened structure of the methylated stretch of the genome and consequently inhibition of its transcription. Thus, heavily methylated parts of the genome are usually not transcribed into mRNA (silenced). This mechanism is an important part of gene regulation and imprinting and one of the central biological features that determine the critical steps in a living cell (Collas et al., 2007). The detail impact of methylation in differentiation processes has only very superficially been investigated so far (Kiefer, 2007). However, more detailed insight has been gathered during the transformation processes that are involved in the transformation of a normal cell into a full blown neoplastic cancer cell (Esteller, 2007; Feinberg, 2004). Particularly for genes with important tumor suppressive activities methylation of the promoter regions have been observed that resulted in reduced expression of the respective genes in the emerging cancer cells. Hence methylation is one of the central molecular steps in the inactivation of tumor suppressor gene besides deletion and/or mutation and has been clearly been proven for many tumor suppressive genes as for example the cyclin dependent kinase inhibitor $p16^{INK4a}$, the DNA mismatch repair genes MSH2, MHL1, and others (Esteller, 2007; Feinberg, 2004).

Besides its impact on the chromatin structure, more refined methylation of distinct nucleotides may also affect the binding properties of certain transcription factors (Klose and Bird, 2006). It thus may influence the affinity of positive or negative acting transcription factors and thus modifies the action and activity of the transcription factors which again results in either more active or reduced expression of the respective genes.

Human papillomaviruses are important epitheliotropic viruses that cause epithelial proliferations of the skin or mucosal surfaces. They attracted particular scientific interest when it became clear, that certain distinct types (high risk papillomaviruses, HR-HPVs) are associated with neoplastic lesions particularly of mucosal surfaces of the genital tract and most importantly of the uterine cervix (zur Hausen, 2002). It is generally accepted today that persistent infections of HR-HPV types (particularly HPV 16 and 18) are an essential prerequisite for the development of cervical cancer. Certain viral genes referred to as E6 and E7 were shown to be continuously expressed in cervical and other HPV-associated cancer cells. They further were shown to induce neoplastic transformation in in vitro cultured primary human epithelial cells and importantly, their expression is essentially required to induce and maintain the neoplastic growth features of cervical carcinoma cells or their high grade precursors.

Up to now, about 13 high risk HPV types have been characterized (Munoz et al., 2003). These viruses are commonly found also in women who have (not yet) developed any clinically detectable lesions. The peak incidence of the virus infections is found in young women at the ages of 15 to 30 years of life, whereas it declines in women of older age (Schiffman et al., 2007). This clearly points to the sexually transmitted characteristics of HR-HPV-infections that are also found in young men at comparable frequencies. The major difference between both genders however is that in males HR-HPV infections usually induce subclinical infections that are rarely realized by the host and that do not progress into invasive cancers, whereas in women long persisting infections apparently occur at substantially higher frequencies that can result in neoplastic transformation of the epithelial cells at the uterine transformation zone that finally may progress into invasive cancers. Interestingly this phenomenon seems to be restricted largely to few epithelial cells that occur at the transformation zone of the uterine cervix, whereas epithelial sites that are infected at comparable rates are substantially less prone to neoplastic transformation in comparison to epithelial cells of the uterine transformation zone.

During their normal life cycle HPVs infect first basal and parabasal cells of the epithelium. Several lines of arguments suggest that they first initiate a state of latent infection (Longworth and Laimins, 2004). During this the viral genome is replicated at very low copy numbers in single infected cells once the host cell divides, however no replication of the viral genome or even lytic infection is initiated at this stage. Due to technical limitations there is no true proof for the existence of this type of latent infection yet. It is anticipated rather from epidemiological studies that show that upon immunosuppression viral replication activity can be reactivated even if there is no evidence for de novo infections. These latent infections apparently can switch into active replicating infections. Here little viral gene expression activity is maintained in basal and parabasal cells, however, once the infected epithelial cells start to differentiate and reach the intermediate cell layers of the epithelium increasing gene expression is observed that triggers replication of the viral genomes in these differentiated cell layers. Interestingly, replication of viral genomes and expression of the viral early genes appears to be largely restricted to terminally differentiated cells that have irreversibly lost the capacity to proliferate and activated gene expression signatures of terminally differentiated epithelial cells that drive them into the pre-programmed pathway of differentiation and finally decay as squamous cell debris at the outer surface of the epithelium (Longworth and Laimins, 2004). Upon replication of the viral genomes in intermediate cells and once the epithelial cells reach during the normal differentiation processes the superficial cell layers, the viral genome again becomes re-programmed and expression of all early genes is stopped, whereas now full blown expression of the late genes L1 and L2 is observed that results in translation of the respective capsids proteins. These aggregate spontaneously to viral capsids in that the replicated viral genomes are included and finally the newly synthesized mature viral capsids are released from the decaying squamous cell debris at the outer surface of the epithelium and can re-initiate further infection cycles (FIG. 1). These findings suggest that the viral replication cycle is strictly linked to the differentiation processes of the normal epithelium. However, since the molecular events that trigger the differentiation of the epithelial cells, little or nothing is so far known about the molecular features that are involved in the regulation of the viral gene expression patterns that control this complex replication process.

Critical structures for the regulation of the viral gene expression as well as for the replication of the viral genomes are retained in a sequence element referred to as long control region (LCR) or upstream regulatory region or (URR). In this element various binding sites for important positive and negative transcription factors as well as the origin of replication are found (FIG. 2).

The papillomavirus E2 protein that is part of the several early expressed papillomavirus genes has substantial inhibitory functions on the expression of viral genes by binding to the viral promoter itself (Wells et al., 2000). It thus acts as a transcriptional repressor and prevents transcription of genes under control of the HPV URR element. This notion is based on a variety of molecular studies that have been performed in tissue culture models using non-differentiated epithelial cells grown in vitro or even cancer cell lines that retain the quasi non-differentiated phenotype of basal or parabasal cells. Expression of the E2 protein has been shown to result in down-regulation of the viral promoter and cessation of the expression of adjacent genes (Bouvard et al., 1994).

In cervical cancer cells, the papillomavirus genome is usually found to be integrated into host cell chromosomes (Pett and Coleman, 2007b). Whereas the integration site of the viral genome into the host cells genome appears to be randomly selected, is the viral genome of integrated viral DNA fragments usually preserved in a very peculiar manner. First of all are fragments that encompass the URR, and the E6 and E7 genes in all yet analyzed retain in an configuration that would still permit expression the E6 and E7 genes even from integrated viral genome copies, whereas the downstream located genes E2 and the late gene cassette is usually disconnected from the regulatory elements within the URR and hence functionally or even structurally inactivated (zur Hausen, 2002). Interestingly, in all HPV-associated carcinoma cells that have been investigated with this regard, expression of the viral E6 and E7 could be confirmed. As mentioned earlier, these genes confer important growth regulatory features to replicating cells through complex interactions with a number of host cell proteins that at least in part are involved in the regulation of the cell cycle, differentiation processes, and death cascades. The expression of these genes is a critical and sufficient prerequisite to induce and maintain neoplastic transformation of epithelial cells. If the expression of these genes is blocked in transformed cells these cells fall into cell cycle arrest, cease growth and eventually die (von Knebel et al., 1988).

In line with this observation is the open reading frame that encodes the E2 gene of HR-HPV types usually disrupted in HPV associated cancers. Re-introduction of functionally active E2 proteins into HPV-transformed cells therefore results in reversion of the neoplastic phenotype, cell cycle arrest and eventually cell death (Wells et al., 2000).

It is thus generally accepted among scientists in the field that disruption of the E2 ORF by integration into the host cell chromosomes is a critical if not absolutely essential step in the molecular cascade that finally results in malignant transformation of HPV-infected epithelial cells (Pett and Coleman, 2007a; Pett et al., 2006; Pett et al., 2004; Alazawi et al., 2002).

The tight association of the HPV replication cycle with features of epithelial differentiation suggests that the host cell milieu plays a critical role in the control of viral gene expression and replication (see FIG. 1). Several lines of evidence suggest that methylation and other forms of epigenetic regulation are involved in the gene expression and replication regulation of the viral genome. Most of these data are based on artificial tissue culture models. All models so far did not allow explaining the details of the differentiation dependent regulation of viral gene expression and replication.

Methylation of papillomavirus DNA was already described about 20 years ago (Burnett and Sleeman, 1984; Wettstein and Stevens, 1983) Its biological significance, however, in the regulation in papillomavirus gene expression control and the associated carcinogenic effects are still only poorly understood (List et al., 1994; Rost et al., 1993; Thain et al., 1996). It appears that CpG methylation in HPV-16 and HPV-18 genomes occurs more often in LCR regions and part of L1 ORF region than in any other parts of the virus genome in cervical cancer cell lines (Badal et al., 2004; Badal et al., 2003). Moreover, methylation particularly of the L1 gene appears to be associated with integration of the foreign viral DNA into the host cell genome during carcinogenesis and was thus suggested as potential biomarker for neoplastic conversion of HPV-infected cells (Kalantari et al., 2004; Turan et al., 2006). Further data also suggest that CpG methylation in E2BS prevents E2 protein binding in vitro (Thain et al., 1996) and modulates E2 protein function in cells in transcription activation (Bhattacharjee and Sengupta, 2006; Kim et al., 2003). However, DNA methylation in cancers is not restricted to HPV DNA. As outlined earlier, it is regarded as a very important feature, but rather occurs as a frequent event throughout the host genome (Esteller, 2007). The frequency of hypermethylation of many cellular genes has been found being increased significantly with increasing severity of neoplasia (Banno et al., 2007; Dong et al., 2001; Feng et al., 2005; Jeong et al., 2006; Kang et al., 2006; Lai et al., 2007; Lea et al., 2004; Reesink-Peters et al., 2004; Seng et al., 2007; Steenbergen et al., 2004; Virmani et al., 2001; Widschwendter et al., 2004).

A recent study investigated the presence or absence of methlytion of CpGs in E2 binding sites E2BS2 to 4 of HPV 16 in normal epithelium and cervical carcinoma cells (Bhattacharjee and Sengupta, 2006). These authors report that methylation was found in defined CpG islands that are located in the E2BS 2 to 4 proximal to the P97 promoter in the transformed tissues.

However, a clear consistent pattern that would explain distinct biological features with defined changes of the methylation pattern at specific sites could not been delineated in this study.

Kim et at (Kim et al., 2003) reported that hypomethylation was associated with in highly differentiated cell populations of an in vitro tissue culture model using W12 cells. In contrast, the HPV16 LCR from poorly differentiated, basal cell-like cells contained multiple methylated cytosines and were often methylated at E2BSs.

Moreover it has been disclosed in the prior art that human cancers frequently show altered patterns of DNA methylation, particularly at CpG islands. Methylation within islands has been shown to be associated with transcriptional repression of the linked gene. Genes involved in all facets of tumor development and progression can become methylated and epigenetically silenced. Re-expression of such silenced genes can lead to suppression of tumor growth or sensitization to anticancer therapies. Epigenetic agents that can reverse DNA methylation are now undergoing preclinical evaluation and clinical trials in cancer patients. The nucleoside inhibitors 5-azacytidine and decitabine have been tested in many phase I and II trials against many forms of cancer. However, the dose-limiting toxicity for both is myelosuppression, and the most commonly reported non-hematologic adverse effect was nausea and vomiting. Therefore a systemic therapy of cancers with demethylating agents is commonly causing severe side effects.

Specific DNA methylation inhibitors can be used for treating cosmetic and dermatologic conditions. It has been shown that 5 azacytidin inhibits both basal level TGFβ-induced collagen biosynthesis by normal human firoblasts. Collagen has a direct effect on scarring. Hence, inhibition of over-production of collagen in human skin results in inhibition of scar formation. Moreover, the combination of UV treatment and demethylation agent can be used for treatment of cancerous and pre-cancerous skin lesions.

The current invention relates to the finding that methylation of distinct, specific sequence elements within the papillomavirus genome are controlling the viral life cycle, replication and gene expression pattern. Moreover, it relates to the finding that a specific change of this methylation pattern is responsible for the inititiation of the neoplastic transformation induced by some papillomaviruses. This is particularly important for lesions of the mucosal epithelia of body cavities such as e.g. of the uterine cervix, vagina, vulva, anus and of the oropharyngeal tract. To overcome the unwanted and in part unbearable side effects associated with systemic therapies with demethylating agents the inventors found that especially for treatment of HPV related lesions and cancers of the mucosal epithelia of body cavities a topical treatment with demethylating agents may serve as a very effective approach to cure cancers without causing unwanted side effects to the patients.

SUMMARY OF THE INVENTION

The current invention relates to the topical application of demethylationg agents for treatment and/or therapy of lesions of e.g. mucosal epithelia of body cavities. In this respect the present invention further pertains to methods for treatment and therapy of HPV associated lesions. HPV associated lesions comprise e.g. cervical cancer and it's precursor stages as well as warts of the skin.

Further the current invention relates to a pharmaceutical composition comprising a demethylating agent for topical application on mucosal epithelia of body cavities for treatment of HPV related lesions and cancer by preventing viral replication and molecular transition into transforming infections. In this respect the present invention further pertains to a pharmaceutical composition for treatment and prevention of HPV associated neoplasias. The pharmaceutical composition comprises a pharmaceutically acceptable carrier and an epigenetic inhibitor or a demethyaltion agent that interferes with the specific methylation pattern at E2BS1, NFIBS, TEF-1BS and/or SP1 BS.

The present invention also pertains to a method for discriminating latently infected cells from cells with productive HPV infection by determining the methylation pattern of the HPV E2BS1, NFIBS, and/or TEF-1BS (see FIG. 5).

An isolated nucleic acid comprising the sequence of Seq ID 1 to 8, wherein the nucleic acids are methylated at positions given in capital letters in the sequences below.

```
Seq ID 1:
E2BS 1  acCGaattCGgt      from nt 7450 to 7461    CpG 7452, 7458 nt Seq ID 2:
E2BS 2  acCGatttgggt      from nt 7857 to 7869    CpG 7859 nt Seq ID 3:
E2BS 3  acCGaaatCGgt      from nt 35 to 46        CpG 37, 43nt Seq ID 4:
E2BS 4  acCGaaacCGgt      from nt 50 to . . . 61  CpG 52, 58nt Seq ID 5:
NFI  cttgccatgCGtgccaaatc from nt 7541to 7560     CpG 7550nt Seq ID 6:
NFI  aatcactatgCGccaaC    from nt 7663 to 7679    CpG 7673, 7679nt Seq ID 7:
TEF-1 tacatacCGct          from nt 7684 to 7694    CpG 7691nt Seq ID 8:
Sp1 taagggCG               from nt 25 to 32        CpG 31nt
```

For the above Sequences all nucleotide positions are cited according to full-genome HPV 16 sequence NCBI Acc. N NC_001526. The C given in capital letters correspond to methyl Cytosine. The G given in capital letters indicate sites where on the reverse complementary strand a methyl-cytosoine is located.

An isolated nucleic acid of Seq ID 9 to 15 below

```
Seq ID 9:
E2BS 1 atTGaattTGgt

Seq ID 10:
E2BS 2 atTGatttgggt

Seq ID 11:
E2BS 3 atTGaaatTGgt

Seq ID 12:
E2BS 4 atTGaaatTGgt

Seq ID 13:
NFI tttgttatgTGtgttaaatt

Seq ID 14:
NFI aattattatgTGttaaT

Seq ID 15:
TEF-1 tatatatTGtt

Seq ID 16:
Sp1 taagggTG
```

DETAILED DESCRIPTION OF THE INVENTION

Figure 1:
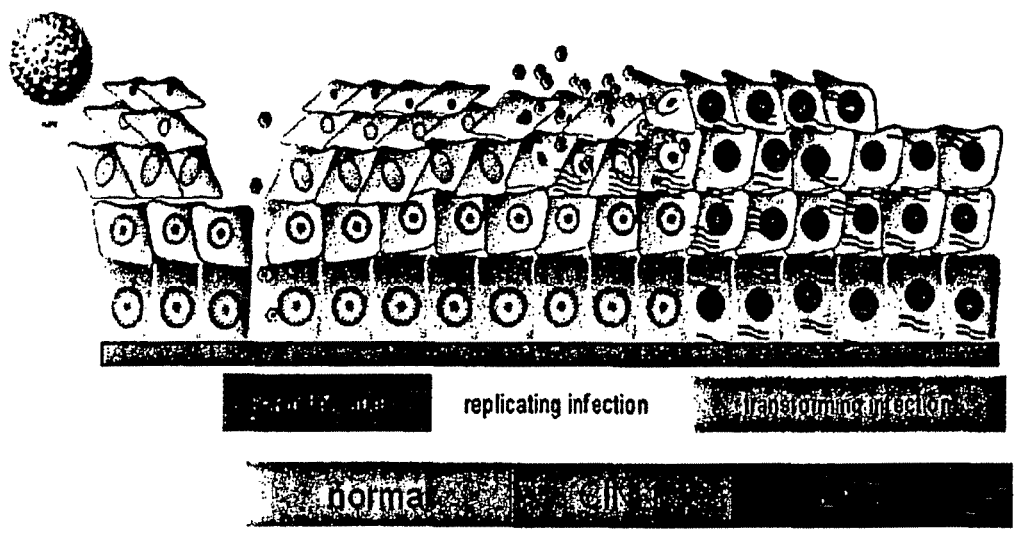
FIG. 1: Schematic representation of the viral life cycle and progression to transforming infections.
Figure 2:
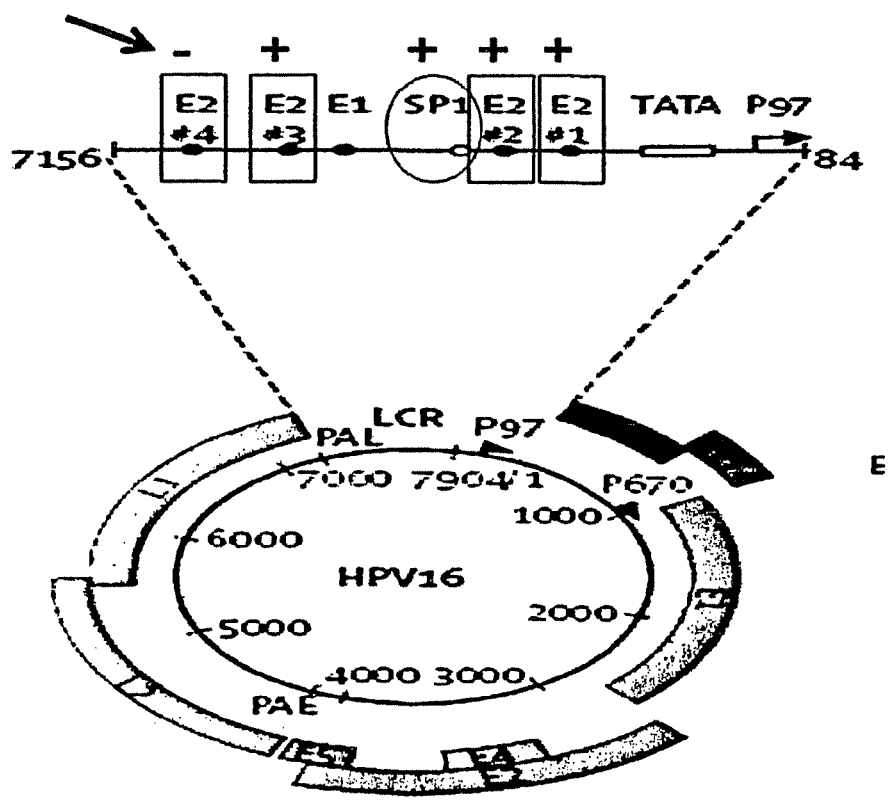
FIG. 2: Schematic representation of the HPV 16 genome and enlargement of the structure of the long control (LCR) or upstream regulatory region (URR). The relative location of the binding sites for the viral E2 protein and the SP1 transcription factor are indicated.
Figure 3:
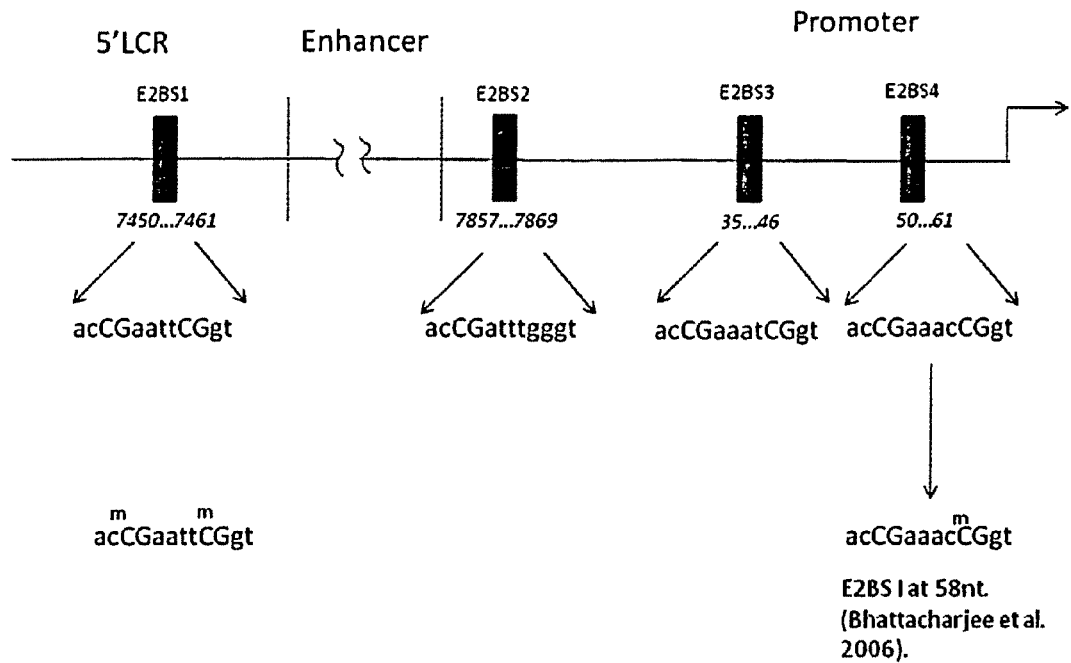
FIG. 3: Schematic representation of the analysis of the methylation pattern as described by (Bhattacharjee and Sengupta, 2006) who compared the methylation pattern of E2BS 4 between normal and neoplastic epithelium and our results that revealed major differences between non-transformed and transformed (p16INK4a-positive) epithelium in E2BS1.
Figure 4:
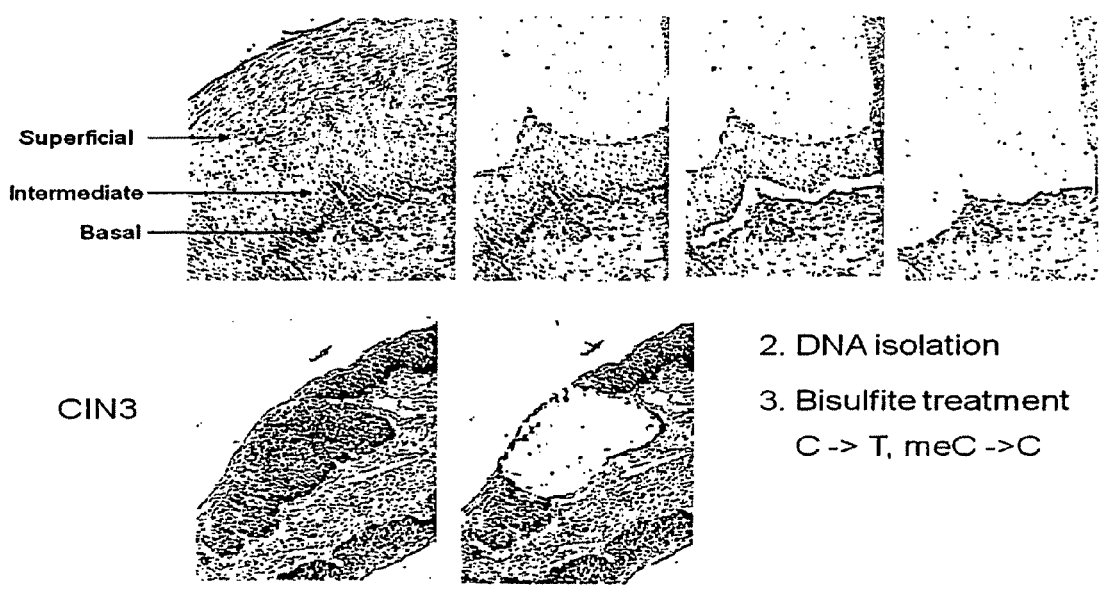
FIG. 4: Example of microdissected cervical epithelium; upper panel: epithelium upon early HPV-infection (emerging evidence of CIN 1), however not transformation and hence not staining for p16INK4a; lower panel: high grade squamous intraepithelial lesion with deregulated HPV E6/E7 oncogene expression and evidence for high grade squamous intraepithelial lesion (HSIL).

The inventors have investigated the methylation pattern of human papillomavirus genomes, in particular the methylation pattern of the URR including its cognate E2BS during three postulated phases of the viral life cycle, i.e. a. latent infection, b. replicating infection, and c. transforming infection. To determine the detailed methylation status of HR-HPV genomes within epithelial cells of different differentiation stages, tissues were micro dissected (see FIG. 4) and HPV sequences were amplified from the different cell layers to allow a precise assessment of distinct methylation patterns of the HPV genome using bisulfite sequencing PCR (BSP) (see FIG. 5).

HPV associated lesion as used here refers to lesions induced by HPV infections encompassing all alterations of any epithelium induced by either acute or persistent HPV-infections. These may range from small warts without clinical impact, rather exophytic growing papillomas, condylomata including inverted papillomas, on the skin, the genital tract, the mucosal surfaces etc. as well as pre-neoplastic and invasive lesions induced by oncogenic papillomavirus genotypes including metastasis derived thereof. Many of the HPV-induced pre-neoplastic or neoplastic lesions occur at the transition zone of different epithelial tissues, particularly where a single layer glandular epithelium meets a multilayered squamous epithelium as for example at the cervical transformation zone, the junction of the rectal mucosa with the anal epithelium, or within the oropharynx in the area of the tonsils.

The inventors to the present invention have found that in normal epithelium that has not yet been affected by cytopathic effects of the HPV, viral genomes may persist in basal cells, clearly demonstrating that there is a latent stage of virus infection in basal and parabasal cells (data not shown). Viral genomes in this latent stage are completely methylated in all CpGs that could be analyzed, suggesting that overall methylation of the viral genomes mediates the latency of the infection and prevents viral gene expression thereby also preventing cyto-pathological or histopathological alterations of the infected epithelium. Thus the inventors found that there is a link between the methylation status of HPV genomes and the latent mode of infection. It is important to note that at this stage methylation was also found in the E2BS1.

Figure 5:
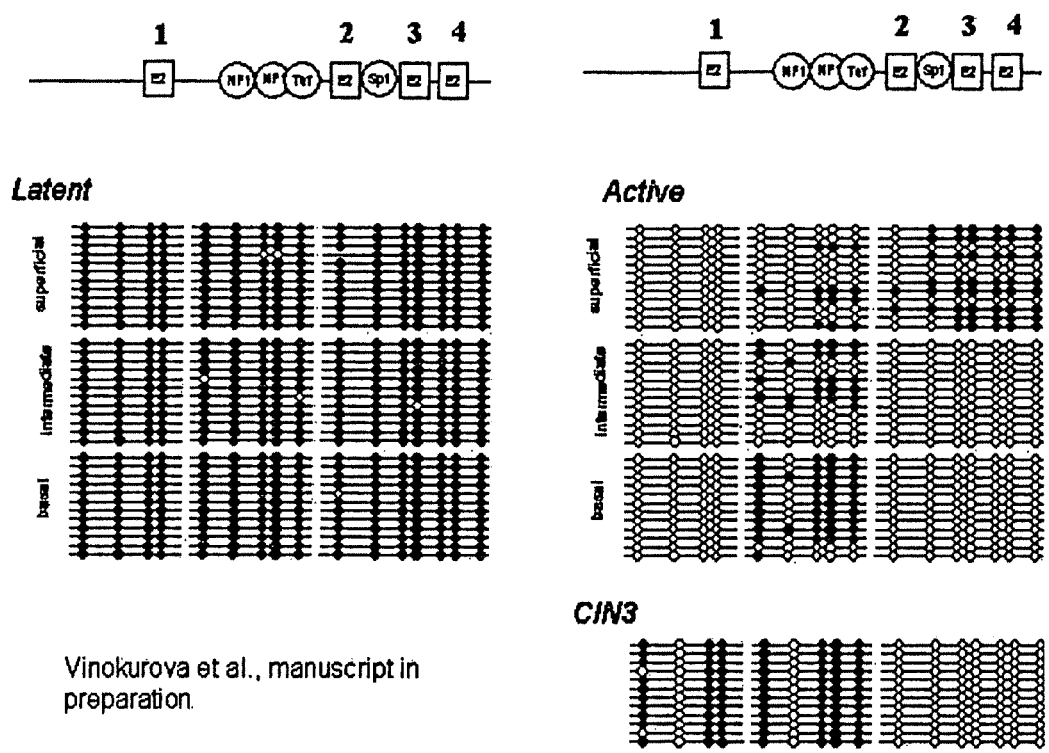
FIG. 5: Schematic representation of the methylation pattern of critical transcription factor binding sites within the HPV 16 URR.

If viral genomes were isolated from micro-dissected cells of early dysplastic lesions (CIN1) distinct changes of the methylation pattern were observed depending on the differentiation status of the host cell and the respective CpG within the viral genome (see FIG. 5). In the basal cell layers, unmethylated E2BSs (1-4) in distinct parts of the URR were observed. Interestingly the E2BS1 was not methylated allowing presumably for binding and repression of the viral enhancer element. If viral DNA was isolated from the intermediate cell layers parts of the genome become de-methylated. This allows access of positive transcription factors (TF) like NFI, TEF-1, and others to stimulate the expression of viral genes. Enhanced viral gene expression results in line with increasing de-methylation in differentiated cells and thus initiation of viral genome replication (FIG. 5).

In the superficial cell layers, all CpG within the early promoter including E2 (E2BSs 2,3 and 4) and SP1 binding sites were methylated, suggesting inactivation of the early promoter activity.

In lesions that progressed already to high grade squamous intraepithelial lesions (HSIL) that therefore show abundant expression of the viral oncogenes E6 and E7 highlighted by the overexpression of the p16$^{INK4a}$ marker (Klaes et al., 2001) (see FIG. 4), consistent methylation of the E2BS1 was observed (FIG. 5). This suggests that by preventing access of the E2 protein to this particular binding site, methylation abolishes the negative transcription regulation and allows for uncontrolled high level of viral gene expression mediated by the HPV 16 URR (LCR).

This methylation pattern was compared between p16$^{INK4a}$ positive parts of the lesions that display deregulated E6 and E7 oncogene expression and the HPV infected but p16$^{INK4a}$ negative part of the lesion that apparently still retain restricted HPV E6 and E7 gene expression lesions using the Combined Bisulfite Restriction Analysis (COBRA) (Xiong and Laird, 1997). The data presented in FIG. 6 support the notion that methylation of the E2BS1 goes along with deregulated expression of the viral oncogenes.

The E2 binding Sites are defined as follows:

```
E2BS 1 acCGaattCGgt
from nt 7450 to 7461      CpG 7452, 7458 nt

E2BS 2 acCGatttgggt
from nt 7857 to 7869      CpG 7859 nt

E2BS 3 acCGaaatCGgt
from nt 35 to 46          CpG 37, 43nt

E2BS 4 acCGaaacCGgt
from nt 50 to . . . 61    CpG 52, 58nt
```

BS positions according to full-genome HPV 16 sequence NCBI Acc. N NC_001526.

Figure 7:
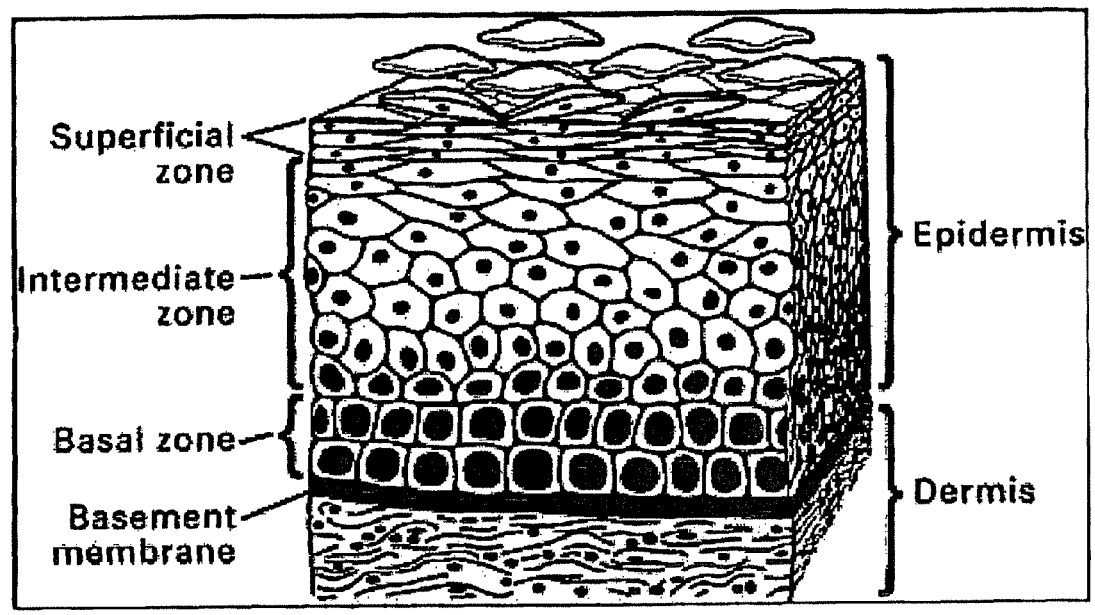
FIG. 7: Structure of Normal Squamous Epithelium [KossLG, et al, 1999]

The normal epithelium may be described as depicted in FIG. 7. The outermost layer of the skin and mucosa consists of multiple epithelial cell layers distinguished by a progressive change in morphology that can be divided into three principal zones (FIG. 20) [Koss L G, et al; Introduction to Gynecologic Cytopathology with Histologic and Clinical Correlations, 1999:23-30.]:

The basal zone consists of one or two layers of low differentiated basal cells (stratum basale) that are spherical and have relatively large nuclei. In normal squamous epithelium, the basal stem cells are the only cells capable of dividing. The basal cells are attached to the basement membrane which separates the epidermis from the dermis.

The intermediate zone of the epithelium represents the bulk of the epithelial thickness and consists of several layers of cells (the para-basal layer or stratum spinosum and the intermediate squamous layer or stratum granulosum) that increase in size toward the surface. Once no longer attached to the basement membrane, these cells exit the cell cycle, stop dividing, and begin to differentiate.

The superficial zone includes rows of larger, flattened cells (mature squamous layer or stratum corneum) with small condensed nuclei and cytoplasm filled with glycogen. The outer layer of the superficial zone consists of terminally differentiated cell.

The analysed region between genomic positions 7198 and 161 contains 16 CpGs (FIG. 5). The analysed region can be divided into 3 functionally distinct segments, which have called the 5'LCR, enhancer and promoter. The 5'LCR contains 4 CpG including CpGs (nt7452, nt7458) within E2BS1 (7450-nnnnn-7461). The enhancer contain five CpGs including 4 CpGs (nt7550, 7673, 7679 and 7691) within NFIBS (7541-cttgccatgCGtgccaaatc-7560; 7663-aatcactatgCGcaaaC-6379) and TEF-1 BS (7684-tacatacCGct-7694). The last seven CpGs in the promoter, six of them (nt7859, 31, 37, 43, 52, 58) overlap with an Sp1(25-taagggCG-32) and three E2 binding sites (E2BS 2 7857-acCGatttgggt-7869; E2BS 3 35-acCGaaatCGgt-46 and E2BS 4 50-acCGaaacCGgt-61).

In contrast to what has been published in the previous reports, we found that in normal epithelium that has not yet been affected by cytopathic effects of the HPV, viral genomes may persist in basal cells, clearly demonstrating that there is a latent stage of virus infection in basal and parabasal cells (data not shown). Viral genomes in this latent stage is completely methylated in all 16 CpGs that could be analyzed (FIG. 5), suggesting that overall methylation of the viral genomes mediates the latency of the infection and prevents viral gene expression thereby also preventing cyto-pathological or histopathological alterations of the infected epithelium. This observation is new, since up to now, no data have been reported that link the methylation status of HPV genomes with the latent mode of infection. It is important to note that at this stage methylation was also found in the E2BS1.

If viral genomes were isolated from micro-dissected cells of early dysplastic lesions (CIN1) distinct changes of the methylation pattern were observed depending on the differentiation status of the host cell and the respective CpG within the viral genome (see FIG. 5).

In the promoter region, DNAs isolated from the basal cells as well as cell fractions from intermediate layer, of the 12 amplimer clones analysed, all contained unmethylated CpGs. A strikingly different result was observed with HPV16 DNAs isolated from the more differentiated cells of the superficial cell layers. In 8 of the 12 amplimers clones generated from HPV16 DNA isolated from the superficial layer enriched for differentiated cells, CpGs within the promoter including E2BSs (2,3 and 4) and SP1 site, were methylated.

In the enhancer region the 4 CpGs within two NFIBSs and one TEF-1BS were heavily methylated in the basal cells but show a lower degree of methylation in the more differentiated cells. This allows access of positive transcription factors (TF) like NFI, TEF-1, and others to stimulate the expression of viral genes. Enhanced viral gene expression results in line with increasing de-methylation in differentiated cells.(FIG. 5).

In the 5'LCR segment all 4 CpGs were unmethylated irrespective of differentiation stage. Interestingly the E2BS1 was not methylated allowing presumably for binding and repression of the viral enhancer element.

In lesions that progressed already to high grade squamous intraepithelial lesions (HSIL) that therefore show abundant expression of the viral oncogenes E6 and E7 highlighted by the overexpression of the p16$^{INK4a}$ marker (Klaes et al., 2001) (see FIG. 4), specific methylation pattern was observed (FIG. 5). In the promoter and enhancer regions 4 CpGs within NFIBS and TEF-1 BS were methylated. In the 5'LCR 3 CpGs were methylated including 2 CpGs within E2BS1. This suggests that by preventing access of the E2 protein to this particular binding site, methylation abolishes the negative transcription regulation and allows for uncontrolled high level of viral gene expression mediated by the HPV 16 URR (LCR).

This allowed us to delineate distinct methylation patterns of the viral genomes with biological properties of the respective viral genomes within these host cell tissues. The key findings of this research are:

In latently infected cells that do not display viral activity, the HPV genome is heavily methylated in almost all, if not all CpG islands, thereby preventing any biologically relevant expression of viral genes. For example, more than 80%, preferably 90%, preferably 95%, more preferably 98% of the CpG islands are methylated in cells of basal zone, intermediate zone and superficial zone. This mediates complete hiding of latent HPV-infections in few epithelial stem cells and that can then persist for undetermined periods of time. (see FIG. 5)

Under yet not characterized conditions, the latent state of HPV-infections in individual cells can switch into a replicating infection mode. In the basal cells, the early HPV promoter (including CpGs within E2BS2,3 and 4 and SP1 binding sites as well as 5' long control region (including E2BS1) contained unmethylated CpGs. Thus, in the enhancer region 4 CpGs within NFI and TEF-1 sites were heavily methylated. This pattern of methylation suggests low activity of the p97 promoter. (FIG. 5)

In intermediate cells, the HPV enhancer shows a lower degree of methylation in the more differentiated cells as compared to basal cells, leading to increased activity of the p97 promoter due to binding of the transcription activators such as nuclear factor I (NFI) and transcriptional enhancer factor TEF-1. However, activity of the early promoter is retained on a certain level owing to E2 negative control. (E2BS1 demethylated).

In the terminally differentiated superficial cells, all CpG within the early promoter in including E2 (E2BSs 2,3 and 4) and SP1 binding sites were methylated, suggesting inactivation of the early promoter activity.

The fact that the methylation state of the viral genome is substantially changed depending on the degree of epithelial differentiation of the host cells suggesting that DNA methylation have important roles in the viral life cycle and presumably also epithelial differentiation. Moreover, functionally distinct, both high- and low-risk virus types may share common mechanisms for regulating their productive life cycles.

Upon long persistence of replicating infections, infected cells of the basal and parabasal cells may switch the methylation profile of the basal and parabasal cells into the transforming mode of HPV-infections that are primarily characterized by methylation of the EBS1, nt 7459. Methylation of this CpG-islands results in loss of E2 binding to E2BS1 and interestingly, loss of its inhibitory function on the URR. Consequently, respective HPV genomes loose thereby the intracellular surveillance control and start to express substantial levels of the viral oncogenes E6 and E7 in the basal cell compartment.

Mapping of methylated CpGs in the URR of HPV16 by bisulfate genomic sequencing (BGS) technique.

DNA isolated from laser-microdissected cells with different degree of differentiation (basal, intermediate and superficial layers) was analysed for the methylation status of the URR of HPV16 using bisulfite genomic sequencing (BGS).

Bisulfite modification of DNA was carried using the EZ DNA methylation kit (Zymo Research, Orange, Calif.) according to the manufacturer's recommendations. DNA from the Caski and SiHa cell lines was used as control and treated concurrently with the samples to ensure complete bisulfite treatment.

A nested BSM-PCR system was developed and performed using the primers design to span the URR of HPV16 (from nt 7198 to nt 161; NC_001526) (Table1).

| | Primer | Sequence 5' to 3' |
|---|---|---|
| 5' LCR | 5' LCR16_for | TTTGTATGTGTTTGTATGTGT |
| | 5' LCR16_rev1 | TTAAACCATAATTACTAACATAA |
| | 5' LCR16_rev2 | ACATTTTATACCAAAAAACATA |
| Enhancer | Enh16_for | TAGTTTTATGTTAGTAATTATGGTT |
| | Enh16_rev1 | ATTAACCTTAAAAATTTAAACC |
| | Enh16_rev2 | AAAAATTTAAACCTTATACCAA |
| Promoter | Prom16_for1 | TTGTATGTGTTTGTATGTGT |
| | Prom16_for2 | GGTTTAAATTTTTAAGGTTAAT |
| | Prom16_rev | ACAACTCTATACATAACTATAATA |

PCR reaction mixtures were performed in a total of 50 µl containing 10×PCR buffer, 5 µl 50 mM MgCl2, 0.5 µl 2 mM deoxynucleotide triphosphates, 0.5 mM of each PCR primer (1.5 µl primer (25 µmol/µl)), 2.0 U Platinum Taq (Invitrogen) and 2 µl of the bisulfite modified DNA. Negative controls without DNA were included in each analysis. Amplification conditions were as follows: initial denaturation at 94° C. for 2 min followed by 40 cycles and 30 cycles for the nested PCR of 94° C. for 30 s, annealing at 50° C. for 30 s, extension at 72° C. for 40 s and finally 72° C. for 4 min. PCR products were separated via electrophoresis and isolated from 2% agarose gels stained with ethidium bromide. Isolated PCR products were then purified by QIAquick Gel Extraction Kit (Qiagen, Hilden) according to the manufacturer's instructions. Purified PCR fragments were cloned the TA Cloning System (Invitrogen) and 12 individual clones were sequenced to identify the presence and patterns of methylated CpGs within HPV16 DNA Sequencing of bisulfite modified sample DNA was performed using the BigDye terminator sequencing kit (Applied Biosystems, Foster City, Calif.) according to the manufacturer's recommendations. The sequencing PCR products were analyzed on the ABI Prism 310 Genetic Analyzer.

Determination of methylation status of HPV16 E2BS1: the Combined Bisulfite Restriction Analysis (COBRA)

In order to determine the methylation status of the E2BS-1 [7450-acCGaattCGgt-7461], distal to P97 promoter of HPV16 we used the Combined Bisulfite Restriction Analysis (COBRA.) (Xiong and Laird, 1997).

DNA isolated from p16-positive and p16-negative lesions was bisulfite treated using the EZ DNA methylation kit (Zymo Research, Orange, Calif.) according to the manufacturer's recommendations.

After treatment, 5 µl of aliquot were amplified in 50 µl of solution containing 1× buffer, 1.25 mM deoxynucleotide triphosphate mixtures, 2.5 µmol of each primer, and 1.5 unit of Taq DNA polymerase (Life Technologies, Inc.). PCR was carried out as follows. After a hot start, the cycling parameters were: 94° C. for 30 s, 50° C. for 30 s, and 72° C. for 60 s for 45 cycles and final elongation at 72° C. for 4 min. Primers used for COBRA were as follows: mHPV16_E2BS1 for 5'AATTGTGTTGTGGTTATTTATTG3' and mHPV16_E2BS1rev 5-CAAATTTAAACCATAATTAC-TAAC3'.

Figure 6:
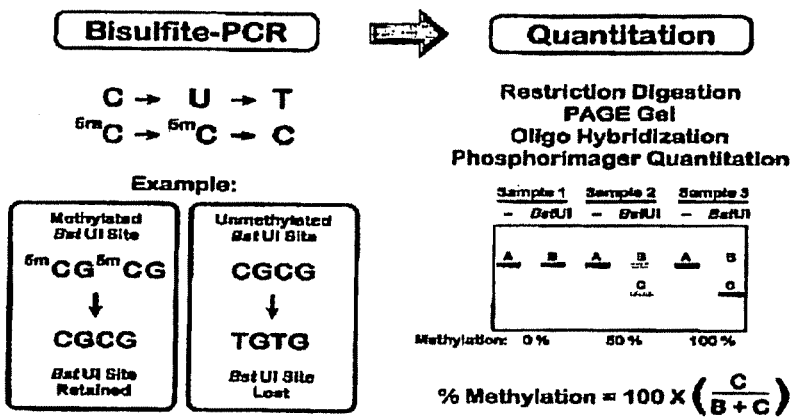
FIG. 6: Principle of the COBRA-Assay and the results of the analysis of some clinical samples of the E2BS1 of the HPV 16 genome.
Figure 6:
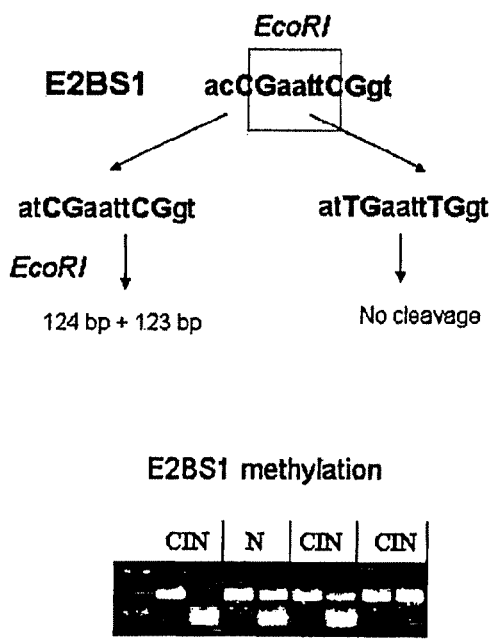

After amplification, PCR products were digested with the restriction enzyme EcoRI (New England Biolabs). The EcoR I recognizes E2BS1 sequences unique to the methylated and bisulfite-converted DNA (FIG. 6). DNA was electrophoresed in 2% agarose gels. The gels were stained with ethidium bromide.

We can explain tissue specificity. Since HPVs need specific methylation machinery to support their viral cycle.

These data suggest that the methylation state of the viral genome is substantially changed depending on the degree of epithelial differentiation of the host cells. Moreover, our results indicate that E2 binding site 1 methylation might play an important role in the initial stage of cervical cancer progression.

Therefore, the use of demethylating agents that could disturb normal viral cycle and will eventually be a more rational Demethylating agent as used herein may be any agent affecting the methylation status of nucleic acids and may be e.g. 5-Azacytidine (Vidaza), 5-Aza-20-deoxycytidine (Decitabine, dacogen), Arabinosyl-5-azacytidine (Fazarabine) 5-6-Dihydro-5-azacytidine (DHAC) 5-Fluoro-20-deoxycytidine (Gemcitabine), Epigallocatechin-3-gallate (EGCG), Hydralazine, Procainamide, Procaine, Zebularine, or a combination thereof. Another classes of demethylating agents are specific oligonucleotides (for example EGX30P), specific RNAi or DNMT1 antisense (MG98). In a preferred embodiment, 5-azacytidine, 5-aza-2-deoxycytidine, or a combination thereof is utilized.

A Pharmaceutical composition for topical administration according to the present invention may be provided in formats like aerosols, cream, gel, liquid, ointment, paste, patch, tampons, caps and any other device and or formulations for controlled release of demethylating agents.

Pharmaceutical compositions according to the present invention may additionally comprise active ingredients. Active agents of the invention can be used to provide controlled release pharmaceutical formulations containing as active ingredient one or more compounds of the invention in which the release of the active ingredient can be controlled and regulated. Control release compositions may be achieved by selecting appropriate polymer carriers such as for example poly(dimethylsiloxane), ethylene vinyl acetate copolymers, polycarophil, hydroxypropyl methylcellulose and polyacrylic acids. The rate of drug release and duration of action may also be controlled by incorporating the active ingredient into particles, e.g. microcapsules, of a polymeric substance such as hydrogels, and the other above-described polymers. Controlled release may be achieved by methods that include colloid drug delivery systems like liposomes, microspheres, microemulsions, and others.

The demethylating agents may be e.g. 5-azacytidine or 5,6-Dihydro-5-azacytidine hydrochloride. Also a chemically stable, soluble analog of 5-azacytidine, can be used in a hydrophilic cream base or hydrophilic gel base. For example, 1% cream is a topical preparation containing 5-azacytidine 1% w/w or 5,6-Dihydro-5-azacytidine hydrochloride, 1% w/w in a hydrophilic cream base containing stearic acid, Aquaphor®, isopropyl palmitate, polyoxyl 40 stearate, propylene glycol, potassium sorbate, sorbic acid, triethanolamine lauryl sulfate, and purified water.

Additives may also include buffers (such as sodium phosphate), humectants (such as glycerin or sorbitol) and other excipients known to those skilled in the art. 1% aqueous gel contains 1% w/w 5-azacytidine or 1% w/w or 5,6-Dihydro-5-azacytidine hydrochloride in a base of betadex, edetate disodium, hydroxyethyl cellulose, methylparaben, niacinamide, phenoxyethanol, propylene glycol, propylparaben and purified water. 5-azacytidine (1%) hydrophilic gel can be prepared by incorporating 1% 5-azacytidine by weight into hydroxyethylcellulose, Natrosoll 1% solution in distilled water.

The principal may be applied to a combination of different active agents of the invention or to a combination of the different active agents of the invention with other drugs that exhibit anti-HPV activity.

While it is possible for the demethylating agents to be administered alone it is preferable to present them as pharmaceutical formulations. The pharmaceutical compositions of the present invention comprise a) a demethylating agent and b) a pharmaceutically acceptable carrier.

In another embodiment the pharmaceutical composition comprises a) a demethylating agent, b) an antiviral agent to provide a synergistic effect against a viral infection, and c) a pharmaceutically acceptable carrier.

5-azacytidine, 5-aza-2-deoxycytidine, or a combination thereof may be prepared into various pharmaceutical formulations which are presently known or may be developed in the future.

In certain embodiments 5'-Azacytidine is applied in topical pharmaceutical compositions at a concentration of 0.001%-50% w/w, more preferred of 0.005%-20% w/w, even more preferred of 0.005%-10% w/w. The demethylating agent is a cream comprising a demethylating agent at a concentration of from about 0.001% to 10%.

TABLE 2

|  | Brush % w/w | Tampons % w/w | Cervical caps % w/w |
|---|---|---|---|
| 5`Azacytidine | 0.1-5 | 0.1-1 | 0.1-1 |
| 5,6-Dihydro-5-azacytidine | 1-10 | 1-5 | 1-5 |
| Epigallocatechin 3-gallate (EGCG) | 1-10 | 1-5 | 1-5 |

Application schedules for the different forms are: Brush—every 8 h, Tampons—daily. Cervical cap every 2 days.

Application of 5'-Azacytidine is used at a dosage of 0.1 µg to 100 µg, in another embodiment at a dosage for each single application of 0.5 µg to 50 µg, in yet another embodiment at a dosage of 1 µg to 10 µg in a further embodiment at a dosage of 500 µg to 2 µg. In certain embodiments of the invention 1 dosage per day, two dosages per day, three dosages per day, four dosages per day or even five or more dosages per day are applied. In certain embodiments of the invention the application is designed to be continuous using a medium continuously releasing the demethylating agent. In further embodiments the dosage is given weekly, twice a week, thrice a week, every other week or monthly. Such dosage may be applied for example for a total period of 1 week, of two weeks, of three weeks, four weeks, five weeks, six weeks, two months, three months or even longer. In certain embodiments the period of application may be half a year, one year or even longer.

One example of device that ca be used for drug delivery to the cervix is a cotton swab or brush Other example of device that ca be used for drug delivery is the cervical cap. For example, cavity rim caps adhere to the cervix. The cavity rim caps are Prentif™ Caps. The Prentif™ Cervical Cap covers a patient's cervix and is used as a barrier method of contraception. Similarly, the TodayR™ contraceptive sponge was a sponge-like device shaped to fit over a patient's cervix.

Other types of devices used in connection with a patient's cervix is a vaginal tampon, vaginal ring, vaginal strip, vaginal capsule, bioadhesive film or sponge. Device is incorporated with the composition comprising from about 1 to about 10 mg mg of the epigenetic agent, about 10% of hydroxypropyl methylcellulose, about 70% of saturated triglyceride of fatty acids for a hydrophilic drug or PEG 6000/PEG 400 for a lipophilic drug and about 15% of ethoxydiglycol.

EXAMPLES

Example 1

Detection of Methylation Pattern

To investigate whether methylation of HPV 16 URR is influenced by differentiation status of the host epithelial cells, we analyze HPV16 DNA isolated from laser-microdissected normal epithelial cells with different degree of differentiation using bisulfite genomic sequencing (BGS).

The p97 HPV16 promoter in the basal cells derived from the normal epithelium as well as cell fractions from intermediate layer contained unmethylated CpGs. In contrast, HPV16 promoter in superficial layer enriched for differentiated cells was methylated, including CpGs within E2 (E2BSs 2,3 and 4) and SP1 binding sites. In the enhancer region we found decreased methylation of one CpG site (7454) in all differentiation stages. Thus, the other 4 CpGs (CpG) were heavily methylated in the basal cells but show a lower degree of methylation in the more differentiated cells. 5' LCR region was hypomethylated in all differentiation stages.

We further compare the methylation pattern of HPV16 URR in HSIL lesions with corresponding normal epithelium using over-expression of the cyclin dependent kinase inhibitor p16INK4a as biomarker for HPV-transformed epithelial cells using combined bisulfite restriction analysis (COBRA).

These data indicate that the methylation of the E2BS1 specifically occurs during the transition of replicating to transforming HPV infections.

Example 2

Assessment of Diagnosis 101 samples (smears and punch biopsies), which are derived from cytologically and histologically confirmed low-grade (LSIL, n=53) and high-grade (HSIL, n=48) lesions infected with HPV16 are tested for the presence of the E2BS1 methylation by combined bisulfite restriction analysis (COBRA).

The detection of the specific LCR HPV16 methylation provides a molecular marker for detecting pre-cancerous lesions with high risk for cancer progression.

TABLE 3

|      | Sample N | E2BS1 methylation, (%) |
|------|----------|------------------------|
| LSIL | 53       | 12 (22.6)              |
| HSIL | 48       | 36 (75)                |

Methylation of E2BS1 was present in 75% high-grade lesions but only in 22.6% of low grade intraepithelial lesions. Thus, the detection of the specific LCR HPV16 methylation may provide a molecular marker for detecting pre-cancerous lesions with high risk for cancer progression.

Figure 8:
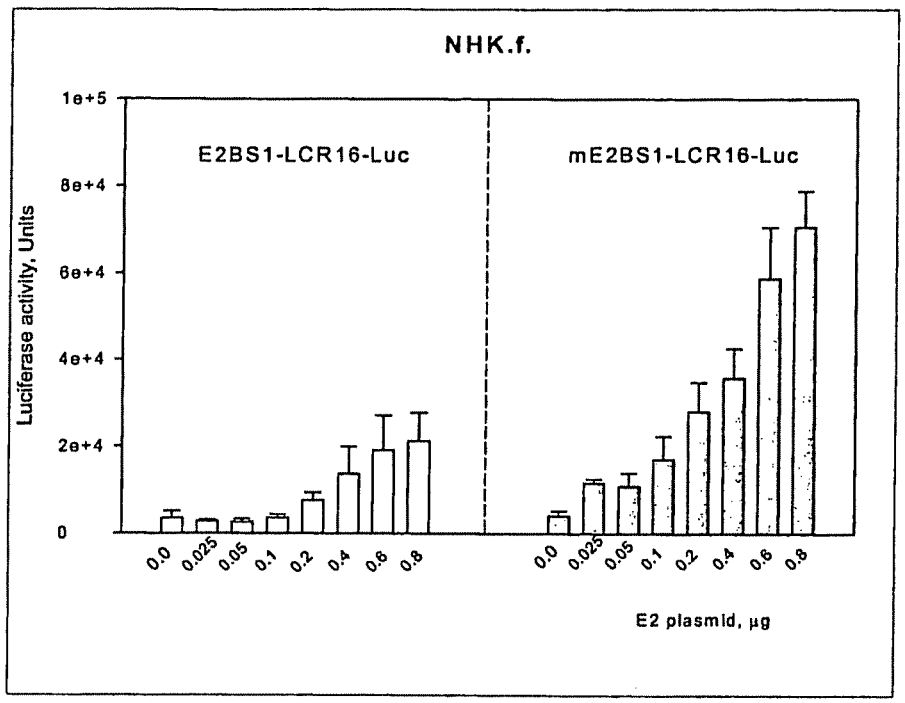
FIG. 8: Effect of E2BS-1 methylation on the p97 early promoter activity.

To verify whether E2 binding to E2BS1 is responsible for the activation of the p97 promoter we analyzed the effect of E2BS1 methylation on the activity of P97 in transient transfection experiments. Selective methylation of the 2 CpG dinucleotides in E2BS1 were introduced into the wild-type HPV16 LCR. We co-transfected normal human foreskin keratinocytes with increasing amounts of an expression vector for HPV16 E2 and about 50 ng of a reporter plasmid containing either the entire HPV16 LCR in front of the luciferase gene (E2BS1-LCR16-Luc) or an LCR with the methylation in E2BS1 (methE2BS1-LCR16-Luc). Methylation of E2BS1 leads to 4-6 fold activation of the early p97 HPV16 promoter (FIG. 8). This data suggest that by modulating of the E2 protein binding to this particular binding site, methylation activates the p97 promoter and allows for uncontrolled high level of viral gene expression.

These data further show, that detection of the specific methylation of E2BS1 can be used to identify lesions that have already undergone the transition from acute to transforming HR-HPV infections. Methylation of the E2BS1 may thus serve as biomarker for HSIL.

Example 3

Therapeutic Application of 5' Azacytidine in Cell Culture

The impact of treatment with epigenetic inhibitors (demethylation agents) on the activity of the p97 promoter is assessed using luciferase assay. Normal human keratinocytes transfected with the reporter plasmid LCR16_Luc, which contains the complete LCR fragment of the HPV-16 cloned in front of the luciferase gene were grown to about 50-60% confluence. Cells were treated with 2 µM and 4 µM 5-azacytidin for 24 and 72 hs. The addition of 5-azacytidine to the cells decreased the activity of the early p97 promoter in a dose dependent manner.

Figure 9:
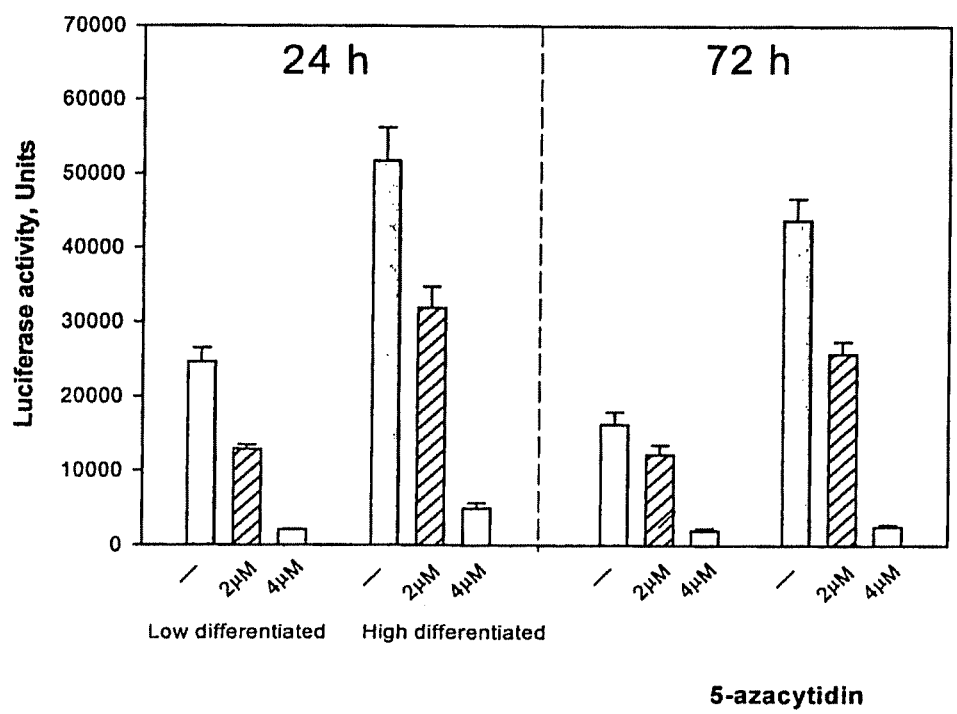
FIG. 9: Effect of 5-azacytidin on the p97 early HPV16 promoter activity

As shown in FIG. 9, when undifferentiated or differentiated cells were treated with 2 µM 5-azacytidin, the p97 promoter activity was reduced to 40-60%). In both cells treated with 4 µM 5'-Azacytidin, the promoter activity was significantly reduced to the basal level.

These data show that application of 5-aza-cytidine as an example for a demethylating agent results in substantial inhibition of the activity of the HPV 16 URR. It therefore has a great potential to block the viral life cycle as well as to prevent the switch from acute to transforming HPV-infections. Based on these data such agents can be used to prevent replication to the virus, and its progression into higher grade dysplasia or even cancer.

What is claimed is:

1. A method for treating an HPV related lesion, comprising administering an effective amount of a demethylating agent to an HPV related lesion of a patient, wherein the HPV related lesion is selected from the group consisting of low-grade lesions, high-grade lesions, condylomas, and warts.

2. The method according to claim 1, wherein the HPV related lesion is a low-grade lesion.

3. The method according to claim 1, wherein the HPV related lesion is a high-grade lesion.

4. The method according to claim 1, wherein the HPV related lesion is a condyloma.

5. The method according to claim 1, wherein the HPV related lesion is a wart.

6. The method according to claim 1, wherein the demethylating agent is 5-azacytidine or 5-aza-2'-deoxycytidine.

7. The method according to claim 6, wherein the demethylating agent is 5-azacytidine.

8. The method according to claim 6, wherein the demethylating agent is 5-aza-2'-deoxycytidine.

* * * * *